United States Patent
Nemoto et al.

(10) Patent No.: US 10,786,219 B2
(45) Date of Patent: Sep. 29, 2020

(54) RADIOGRAPHIC IMAGE PROCESSING APPARATUS, SCATTERED RADIATION CORRECTION METHOD, AND COMPUTER READABLE STORAGE MEDIUM

(71) Applicant: KONICA MINOLTA, INC., Chiyoda-ku, Tokyo (JP)

(72) Inventors: Eri Nemoto, Hino (JP); Ryohei Ito, Hino (JP)

(73) Assignee: KONICA MINOLTA, INC., Chiyoda-Ku, Tokyo (JP)

(*) Notice: Subject to any disclaimer, the term of this patent is extended or adjusted under 35 U.S.C. 154(b) by 67 days.

(21) Appl. No.: 16/255,081

(22) Filed: Jan. 23, 2019

(65) Prior Publication Data
US 2019/0223820 A1 Jul. 25, 2019

(30) Foreign Application Priority Data
Jan. 24, 2018 (JP) ................................. 2018-009644

(51) Int. Cl.
*G01N 5/00* (2006.01)
*A61B 6/00* (2006.01)
*G06T 5/50* (2006.01)

(52) U.S. Cl.
CPC .............. *A61B 6/5282* (2013.01); *G06T 5/50* (2013.01); *A61B 6/5211* (2013.01); *A61B 6/5235* (2013.01); *G06T 2207/20224* (2013.01)

(58) Field of Classification Search
CPC ......... G06T 11/005; G06T 2207/10116; G06T 2207/30004; G06T 7/0012; G06T 5/002; G06T 5/50; G06T 11/008; G06T 11/006; G06T 2207/10016; G06T 2207/20221; G06T 5/003; G06T 2211/416; G06T 2211/424; G06T 2211/436; G06T 2215/16;

(Continued)

(56) References Cited

U.S. PATENT DOCUMENTS

| | | | |
|---|---|---|---|
| 2010/0215243 A1* | 8/2010 | Ohno .................... | A61B 6/4035 382/132 |
| 2012/0243759 A1* | 9/2012 | Fujisawa .............. | A61B 6/5235 382/131 |
| 2014/0056407 A1* | 2/2014 | Goldammer ......... | A61B 6/5205 378/62 |

FOREIGN PATENT DOCUMENTS

| | | |
|---|---|---|
| JP | 09270004 A | 10/1997 |
| JP | 2015100543 A | 6/2015 |

* cited by examiner

*Primary Examiner* — Quan M Hua
(74) *Attorney, Agent, or Firm* — Cantor Colburn LLP (57) ABSTRACT

A radiographic image processing apparatus includes a hardware processor, which determines the intensity of an edge in a radiographic image obtained by radiographically imaging a subject, sets a weighting factor to be used in extracting a frequency component from the radiographic image according to a determination result of the edge intensity, extracts the frequency component from the radiographic image using the weighting factor having been set, multiplies the extracted frequency component by a scattered radiation content rate to estimate a scattered radiation component in the radiographic image, multiplies the estimated scattered radiation component by a scattered radiation removal rate to generate a scattered radiation image representing the scattered radiation component to be removed from the radiographic image, and performs scattered radiation correction on the radiographic image by subtracting the scattered radiation image from the radiographic image.

9 Claims, 9 Drawing Sheets (58) Field of Classification Search
CPC .......... G01N 23/046; G01N 2223/419; G01N 23/04; G01N 2223/402; G01N 23/087
See application file for complete search history.

RADIOGRAPHIC IMAGE PROCESSING APPARATUS, SCATTERED RADIATION CORRECTION METHOD, AND COMPUTER READABLE STORAGE MEDIUM

CROSS-REFERENCE TO RELATED APPLICATION

The present application claims priority under 35 U.S.C. § 119 to Japanese Patent Application No. 2018-009644, filed on Jan. 24, 2018, the entirety of which is hereby incorporated by reference herein and forms a part of the specification.

BACKGROUND

1. Technical Field

The present invention relates to a radiographic image processing apparatus, a scattered radiation correction method, and a computer readable storage medium.

2. Description of the Related Art

Capturing a radiographic image of a subject with radiation transmitted through the subject raises a problem that the radiation scatters in the subject according to the thickness of the subject and generated scattered radiation deteriorates the contrast of the acquired radiographic image. Therefore, at the time of capturing a radiographic image, a scattered radiation removal grid (hereinafter, simply referred to as "grid") can be provided between the subject and a radiation detector so that the radiation detector is not irradiated with scattered radiation when detecting radiation and acquiring the radiographic image. Using the grid to perform imaging can improve the contrast of the radiographic image because the radiation detector is less likely to be irradiated with radiations scattered by the subject. However, using the grid raises a problem that the workload of grid arrangement at the time of portable imaging to be performed in a hospital room or the like is large and the burden on a patient is heavy and further the grid may cut the radiations traveling straight when the applied direction of the radiations is inappropriate. Therefore, in order to improve the contrast lowered by the scattered radiation components of the radiations, it is conventionally known to perform image processing on the radiographic image for correction of the scattered radiation.

For example, Patent Literature 1 (JA2015-100543A) discloses a technique capable of generating a band image that represents a frequency component for each of a plurality of frequency bands by frequency decomposing an original image, converting the band image based on irradiation field information, subject information, imaging conditions and the like and generating a converted band image by multiplying a weight determined for each frequency band, generating a scattered radiation image by combining a plurality of converted band images having been generated, and subtracting the scattered radiation image from the original image to generate a radiographic image from which the scattered radiation has been removed. In general, it is known that the amount of contained scattered radiation is relatively large in a low-frequency band and is smaller in a high-frequency band. Therefore, in Patent Literature 1, the weight is determined so that the weight increases as the frequency band becomes lower.

Further, Patent Literature 2 (JP09-270004A) discloses a technique capable of generating a low-frequency component image by processing an original image with a lowpass filter, adjusting the generated low-frequency component image according to scattered radiation influence degree by the edge, and subtracting the adjusted low-frequency component image from the original image to generate a radiographic image from which the scattered radiation has been removed.

The techniques discussed in Patent Literatures 1 and 2 are techniques based on the recognition that the amount of contained scattered radiation is relatively large in the low-frequency band. However, experiments conducted by inventors of the present invention have revealed that the scattered radiation contains a certain amount of high-frequency components, the amount of frequency components in the high-frequency band increases in the vicinity of strong edges and the amount of frequency components in the low-frequency band increases in the vicinity of weak edges. Therefore, according to the technique discussed in Patent Literature 1 or Patent Literature 2, estimation errors of high-frequency components of the scattered radiation increase, especially, in the vicinity of strong edges, and high-frequency components are more likely to be emphasized after removal of the scattered radiation. Therefore, removal of scattered radiation in the vicinity of edges cannot be precisely performed.

SUMMARY

The present invention intends to obtain a radiographic image from which scattered radiation has been precisely removed by improving the accuracy in estimating scattered radiation in the vicinity of edges in the radiographic image, thereby.

To achieve at least one of the above-mentioned objects, a radiographic image processing apparatus according to one aspect of the present invention includes a hardware processor that determines the intensity of an edge in a radiographic image obtained by radiographically imaging a subject, sets a weighting factor to be used in extracting a frequency component from the radiographic image according to a determination result of the edge intensity, extracts the frequency component from the radiographic image using the weighting factor having been set, multiplies the extracted frequency component by a scattered radiation content rate to estimate a scattered radiation component in the radiographic image, multiplies the estimated scattered radiation component by a scattered radiation removal rate to generate a scattered radiation image representing the scattered radiation component to be removed from the radiographic image, and performs scattered radiation correction on the radiographic image by subtracting the scattered radiation image from the radiographic image.

Further, a scattered radiation correction method according to one aspect of the present invention is a scattered radiation correction method for a radiographic image processing apparatus that performs scattered radiation correction on a radiographic image obtained by radiographically imaging a subject, the method including:

determining the intensity of an edge in the radiographic image, setting a weighting factor to be used in extracting a frequency component from the radiographic image according to a determination result of the edge intensity, extracting the frequency component from the radiographic image using the weighting factor having been set, multiplying the extracted frequency component by a scattered radiation content rate to estimate a scattered radiation component in the radiographic image, multiplying the estimated scattered radiation component by a scattered radiation removal rate to generate a scattered radiation image representing the scattered radiation component to be removed from the radiographic image, and performing scattered radiation correction on the radiographic image by subtracting the scattered radiation image from the radiographic image.

Further, a computer readable storage medium according to one aspect of the present invention is a non-transitory computer readable storage medium storing a program that causes a computer, to be used for a radiographic image processing apparatus that performs scattered radiation correction on a radiographic image obtained by radiographically imaging a subject, to determine the intensity of an edge in the radiographic image obtained by radiographically imaging the subject, set a weighting factor to be used in extracting a frequency component from the radiographic image according to a determination result of the edge intensity, extract the frequency component from the radiographic image using the weighting factor having been set, multiply the extracted frequency component by a scattered radiation content rate to estimate a scattered radiation component in the radiographic image, multiply the estimated scattered radiation component by a scattered radiation removal rate to generate a scattered radiation image representing the scattered radiation component to be removed from the radiographic image, and perform scattered radiation correction on the radiographic image by subtracting the scattered radiation image from the radiographic image.

BRIEF DESCRIPTION OF THE DRAWINGS

The above objects, advantageous effects and features of the present invention will be more fully understood from the following detailed description and the accompanying drawing. However, these are not intended to limit the present invention.

DETAILED DESCRIPTION OF EMBODIMENTS

Hereinafter, one or more embodiments of the present invention will be described with reference to the drawings. However, the scope of the invention is not limited to the disclosed embodiments.

First Exemplary Embodiment

[Configuration of Radiographic Imaging System 100]

Figure 1:
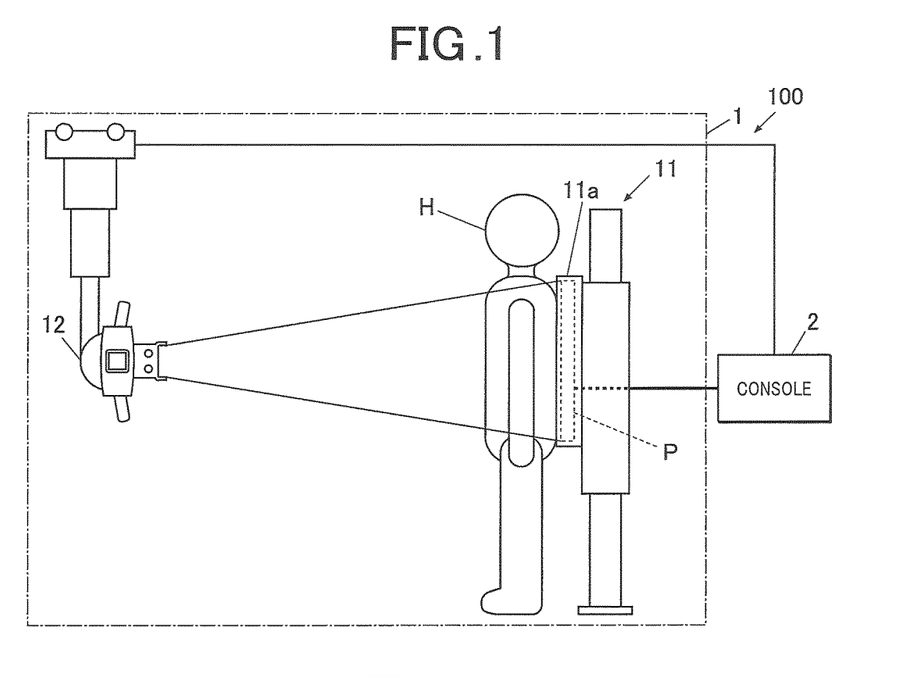
FIG. 1 is a view illustrating the entire configuration of a radiographic imaging system according to an exemplary embodiment of the present invention.

First, a configuration according to the first exemplary embodiment will be described. FIG. 1 is a view illustrating an example of the entire configuration of the radiographic imaging system 100 according to the present exemplary embodiment. As illustrated in FIG. 1, the radiographic imaging system 100 includes an image capturing apparatus 1 and a console 2 that are connected in such a manner that data can be transmitted and received between them.

The image capturing apparatus 1 includes a radiation detector P, an imaging platform 11 on which the radiation detector P is attachable, and a radiation generator 12. The imaging platform 11 includes a holder 11a that holds the radiation detector P.

The radiation detector P is constituted by a semiconductor image sensor, such as flat panel detector (FPD), and is provided so as to face the radiation generator 12 across a subject H. For example, the radiation detector P includes a glass substrate and a plurality of detection elements (pixels) arranged in a matrix pattern, at a predetermined position on the substrate, to detect radiations (X rays) emitted from the radiation generator 12 and penetrating at least the subject H according to their intensities and then convert the detected radiations into electric signals and accumulate them. Each pixel includes a switcher such as a thin film transistor (TFT), for example. The radiation detector P controls the switcher of each pixel based on image reading conditions input from the console 2 to switch the reading of the electric signal accumulated in each pixel and acquires image data by reading the electric signal accumulated in each pixel. Then, the radiation detector P outputs the acquired image data to the console 2.

The radiation generator 12 is disposed at a position where it faces the radiation detector P across the subject H, and performs imaging by irradiating the plurality of radiation detectors P attached to the holder 11a via a patient serving as the subject H with radiations based on radiation exposure conditions input from the console 2. The radiation exposure conditions input from the console 2 include, for example, tube current value, tube voltage value, radiation exposure time, mAs value, and SID (indicating the shortest distance between the radiation detector P and a bulb of the radiation generator 12).

The console 2 outputs imaging conditions, such as radiation exposure conditions and image reading conditions, to the image capturing apparatus 1 to control a radiation imaging operation and a radiographic image reading operation to be performed by the image capturing apparatus 1, and also functions as a radiographic image processing apparatus that performs image processing on a radiographic image acquired by the image capturing apparatus 1.

Figure 2:
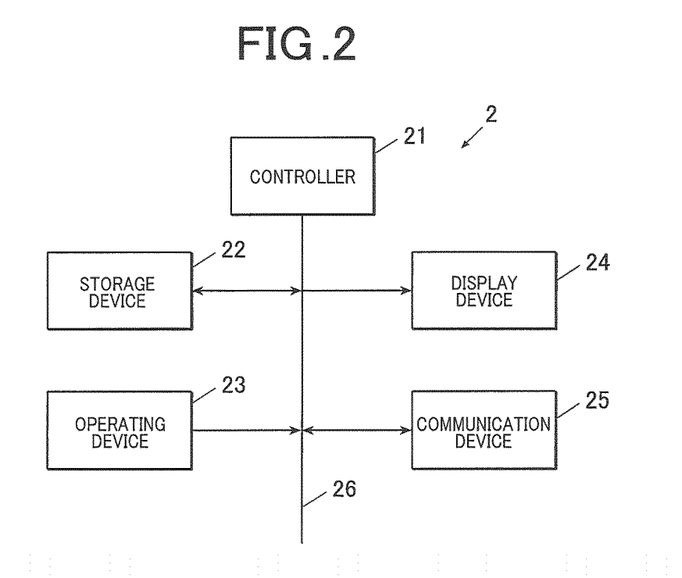
FIG. 2 is a block diagram illustrating a functional configuration of a console illustrated in FIG. 1.

As illustrated in FIG. 2, the console 2 includes a controller 21, a storage device 22, an operating device 23, a display device 24, and a communication device 25, which are mutually connected via a bus 26.

The controller 21 includes a central processing unit (CPU), a random access memory (RAM) and the like. The CPU of the controller 21 reads out system programs and various processing programs stored in the storage device 22 according to an operation of the operating device 23 and develops them in the RAM, and then centrally controls operations to be performed by respective devices constituting the console 2 as well as the radiation exposure operation and the reading operation to be performed by the image capturing apparatus 1 according to the developed programs. Further, the CPU executes image processing, such as scattered radiation correction processing A described below, on a radiographic image transmitted from the radiation detector P of the image capturing apparatus 1.

The storage device 22 is constituted by a nonvolatile semiconductor memory, a hard disk, or the like. The storage device 22 stores various programs to be executed by the controller 21, parameters required in executing each processing by program, and data representing processing results. The various programs are stored in the form of readable program codes, and the controller 21 sequentially executes operations according to the program codes.

In addition, the storage device 22 stores imaging conditions (e.g., radiation exposure conditions and image reading conditions) corresponding to an imaging region. Further, the storage device 22 stores imaging order information transmitted from a radiology information system (RIS) or the like, which is not illustrated. The imaging order information includes patient information, examination information (e.g., examination ID, imaging region (including imaging direction, such as front, side, A→P, P→A, and the like), and examination date).

In addition, the storage device 22 stores a formula (Expression 1) expressing a relationship between pixel value and subject thickness for each imaging condition. Further, the storage device 22 stores a formula (Expression 2) expressing a relationship between subject thickness and scattered radiation content rate for each imaging region.

The operating device 23 is constituted by a keyboard, including cursor keys, numerical input keys, and various functional keys, and a pointing device such as a mouse, and outputs a key operation on the keyboard or an instruction signal input by a mouse operation to the controller 21. Further, the operating device 23 may include a touch panel on a display screen of the display device 24. In this case, the operating device 23 outputs an instruction signal input via the touch panel to the controller 21. Further, the operating device 23 is equipped with an exposure switch for instructing dynamic imaging to the radiation generator 12.

The display device 24 is constituted by a monitor, such as a liquid crystal display (LCD) or a cathode ray tube (CRT), and displays an input instruction from the operating device 23, data, or the like, according to an instruction of a display signal input from the controller 21.

The communication device 25 has an interface that performs transmission and reception of data with each of the radiation generator 12 and the radiation detector P. The communications between the console 2 and the radiation generator 12 or the radiation detector P can be wired communications or wireless communications.

Further, the communication device 25 includes a LAN adapter, a modem, a terminal adapter (TA) and the like, and controls transmission and reception of data with the RIS (not illustrated) or the like connected to a communication network.

[Operations of Radiographic Imaging System 100]

In a state where the radiation detector P is set in the holder 11a of the image capturing apparatus 1, if imaging order information of an imaging target is selected by the operating device 23 in the console 2, imaging conditions (radiation exposure conditions and radiographic image reading conditions) according to the selected imaging order information are read out from the storage device 22 and transmitted to the image capturing apparatus 1. After the positioning of the subject H is completed in the image capturing apparatus 1, if the exposure switch is pressed, the radiation generator 12 emits radiations and the radiation detector P reads image data of a radiographic image. The read image data (i.e., radiographic image) is transmitted to the console 2.

Figure 3:
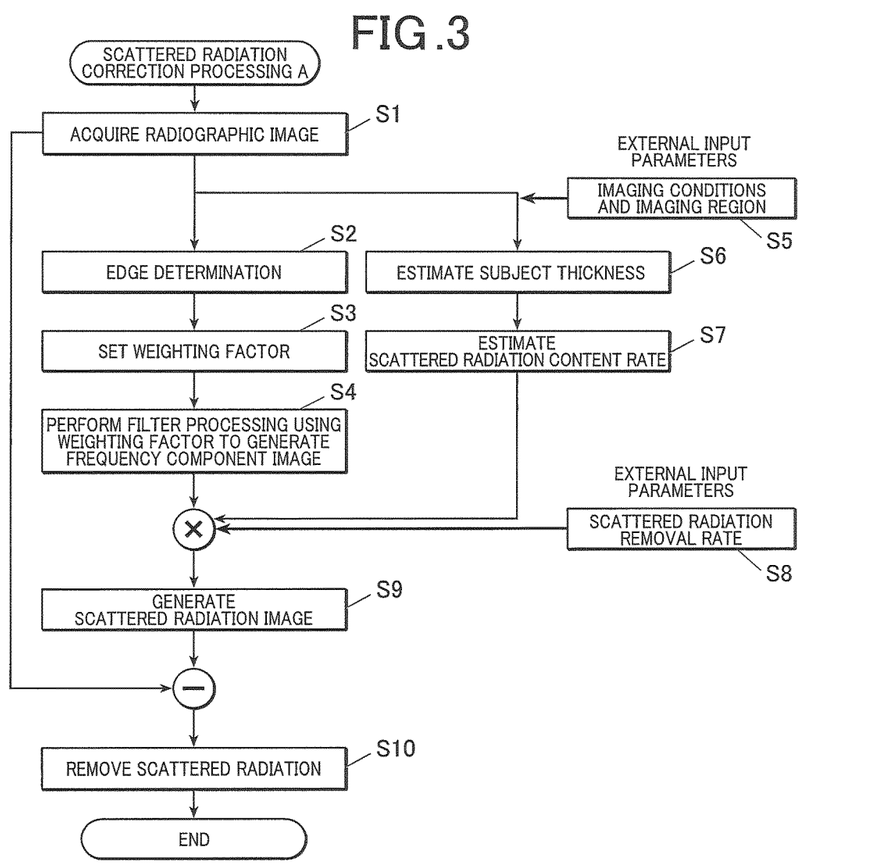
FIG. 3 is a view schematically illustrating an exemplary flow of scattered radiation correction processing A, which can be executed by a controller illustrated in FIG. 2 according to a first exemplary embodiment.

In the console 2, when the communication device 25 receives the radiographic image from the radiation detector P, the controller 21 executes scattered radiation correction processing A. FIG. 3 is a flowchart illustrating an exemplary flow of the scattered radiation correction processing A. The scattered radiation correction processing A can be executed by cooperation between the controller 21 and the programs stored in the storage device 22.

First, the controller 21 acquires the radiographic image transmitted from the radiation detector P via the communication device 25 (step S1).

Next, the controller 21 performs edge determination processing on the radiographic image (step S2).

In the edge determination processing, first, the controller 21 designates each pixel of the radiographic image as an attentional pixel and sets a region of m pixels×n pixels (m and n are positive integers) including the attentional pixel positioned at the center thereof as an edge determination region. The edge determination region is the same as a convolution region (R in FIG. 4) in filter processing to be performed in a subsequent stage. Next, in each edge determination region, the controller 21 calculates a difference between a pixel value of the attentional pixel and a pixel value of each pixel (that is referred to as "referential pixel") in the edge determination region. In this case, the controller 21 can determine that the edge is stronger as the difference between the pixel value of the attentional pixel and the pixel value of the referential pixel is larger. Therefore, in the present exemplary embodiment, the difference between the pixel value of the attentional pixel and the pixel value of the referential pixel is used as a determination result of the edge intensity at the referential pixel. Instead of the difference between the pixel value of the attentional pixel and the pixel value of the referential pixel, a ratio (for example, a ratio having a numerator being the larger one, in this embodiment) may be used.

Next, the controller 21 sets a weighting factor to be used in the convolution calculation during the filter processing based on the edge determination result (step S3).

Figure 5:
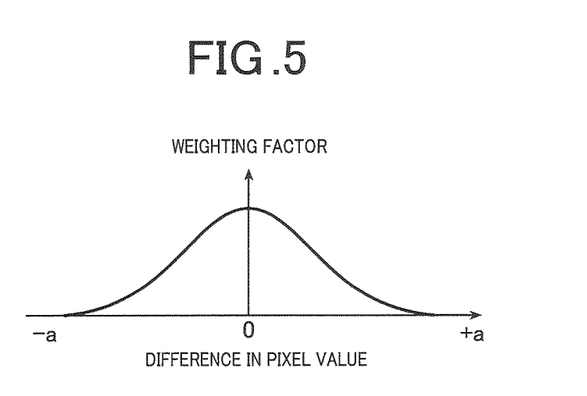
FIG. 5 is a view illustrating a relationship between a weighting factor and a pixel value difference according to the first exemplary embodiment.

In step S3, the controller 21 sets the weighting factor for each referential pixel of each edge determination region. As illustrated in FIG. 5, the setting of the weighting factor is performed in such a manner that the weighting factor becomes larger as the difference (or ratio) in pixel value between the attentional pixel and the referential pixel is smaller (when the edge is weak or there is no edge) and the weighting factor becomes smaller as the difference (or ratio) in pixel value between the attentional pixel and the referential pixel is larger (when the edge is strong). The relationship between the difference (or ratio) in pixel value between the attentional pixel and the referential pixel and the weighting factor can be optimally obtained through experiments and stored beforehand in the storage device 22.

Alternatively, in step S2, the controller 21 can obtain a variance value of the pixel value in the edge determination region and may determine that the edge around the attentional pixel is strong as the variance value is large and also determine that the edge around the attentional pixel is weak as the variance value is small. Further, weighting factors (for example, refer to FIG. 12A to FIG. 12D) differentiated according to the distance between the attentional pixel and the referential pixel can be stored beforehand in the storage device 22. In step S3, the controller 21 can set the weighting factor by adjusting the weighting factor stored beforehand in such a manner that the weight becomes smaller as the edge becomes larger (as the variance value becomes larger) and the weight becomes larger as the edge becomes smaller (as the variance value becomes smaller).

Next, the controller 21 performs filter processing on the radiographic image using the weighting factor having been set to generate a frequency component image (step S4).

Figure 4:
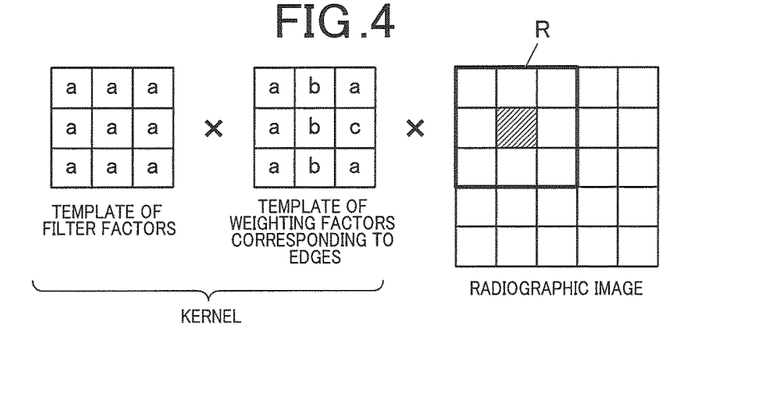
FIG. 4 is a view illustrating filter processing.

In the filter processing, as illustrated in FIG. 4, the controller 21 designates each pixel of the radiographic image as an attentional pixel and sets a region of m pixels×n pixels (m and n are positive integers) including the attentional pixel positioned at the center thereof as a filter region (i.e., a convolution region, indicated by R in FIG. 4). Then, the controller 21 multiplies the pixel value of each pixel in the filter region by an element of the corresponding position in a template of filter factors stored beforehand in the storage device 22 and in a template of the weighting factors set in step S3 and calculates a sum thereof, and then generates the frequency component image by designating the calculated sum as the pixel value of the attentional pixel. The filter factor can be, for example, constant for all elements in the filter region.

Further, the filter factor can be a coefficient (for example, refer to FIG. 12A to FIG. 12D) differentiated according to the distance between the attentional pixel and the referential pixel, and the controller 21 can multiply the pixel value of each pixel in the filter region by an element of the corresponding position in the template of the weighting factors having been set based on an edge determination result determined using the template of the filter factors and the difference or ratio between the pixel value of the attentional pixel and the pixel value of the referential pixel and calculate a sum thereof. Then, the controller 21 can generate the frequency component image by performing bilateral filter processing using the calculated sum as the pixel value of the attentional pixel.

In the filter processing, since the frequency band of a filter processed image is determined by the kernel (i.e., the coefficient to be multiplied with the pixel value in the filter region), performing the filter processing using the kernel obtained by multiplying the filter factor by the weighting factor based on the edge determination result can change the frequency band to be extracted by the location in the radiographic image (the intensity of the edge at the location). As the weighting factor becomes larger, the frequency component of low frequency can be extracted. As the weighting factor becomes smaller, the frequency component of high frequency can be extracted.

Next, the controller 21 acquires imaging conditions of the radiographic image and imaging region information as external parameters (step S5), and estimates the subject thickness from the radiographic image based on the acquired imaging conditions (step S6), and further estimates a scattered radiation content rate from the radiographic image based on the acquired imaging region and the estimated subject thickness (step S7).

The controller 21 acquires the imaging region from the imaging order information used for the imaging and acquires imaging conditions corresponding to the imaging region from the storage device 22. In the present exemplary embodiment, acquired as the imaging conditions are tube voltage, mAs value, and SID. In the present exemplary embodiment, the imaging region and the imaging conditions are acquired based on the imaging order information. However, a user may manually input them from the operating device 23. The imaging conditions may be acquired from the image capturing apparatus 1. Further, the processing in steps S5 to S7 may be executed concurrently with the processing in steps S2 to S4 or may be executed earlier.

The subject thickness of each pixel of the radiographic image can be estimated using the following formula (Expression 1).

Subject thickness=coefficient $A$×log(pixel value)+ coefficient $B$ (Expression 1)

Here, the coefficients A and B are coefficients determined by the imaging conditions (i.e., tube voltage, mAs value, and SID). The above-mentioned formula (Expression 1) is stored in the storage device 22 for each imaging condition.

The method for estimating the subject thickness is not limited to the one described above and a conventionally known method (for example, refer to JP 2016-202219A) may be used.

Further, the scattered radiation content rate of each pixel of the radiographic image can be estimated using the following formula (Expression 2).

Scattered radiation content rate=coefficient $C$×log (subject thickness+coefficient $D$)+coefficient $E$ (Expression 2)

Here, coefficients C, D, and E are coefficients determined by the imaging region. The above-mentioned formula (Expression 2) is stored in the storage device 22 for each imaging region.

Further, the following formula (Expression 3) may be stored in association with the imaging conditions and the imaging region beforehand, and the scattered radiation content rate may be directly obtained from the pixel value using the formula (Expression 3) corresponding to the imaging conditions and the imaging region.

Scattered radiation content rate=coefficient $C$×log (coefficient $A$×log(pixel value)+coefficient $B$+coefficient $D$)+coefficient $E$  (Expression 3)

Next, the controller 21 acquires a scattered radiation removal rate as an external parameter (step S8). For example, a user may input the scattered radiation removal rate from the operating device 23. Further, a value in the range from 0 to 100% entered from the operating device 23 may be acquired as the scattered radiation removal rate. A table indicating a relationship between grid ratio and scattered radiation removal rate may be stored in the storage device 22, and a scattered radiation removal rate corresponding to a grid ratio entered from the operating device 23 may be acquired.

Next, the controller 21 estimates a scattered radiation component by multiplying the scattered radiation content rate for each pixel of the frequency component image generated in step S4 and generates a scattered radiation image representing the scattered radiation amount to be removed from the radiographic image by multiplying the scattered radiation component by the scattered radiation removal rate (step S9).

Then, the controller 21 subtracts the scattered radiation image from the radiographic image (subtracts the pixel value of the corresponding pixel of the scattered radiation image from the pixel value of each pixel of the radiographic image) to generate a radiographic image from which the scattered radiation has been removed (step S10), and then terminates the scattered radiation correction processing A.

Figure 6A:
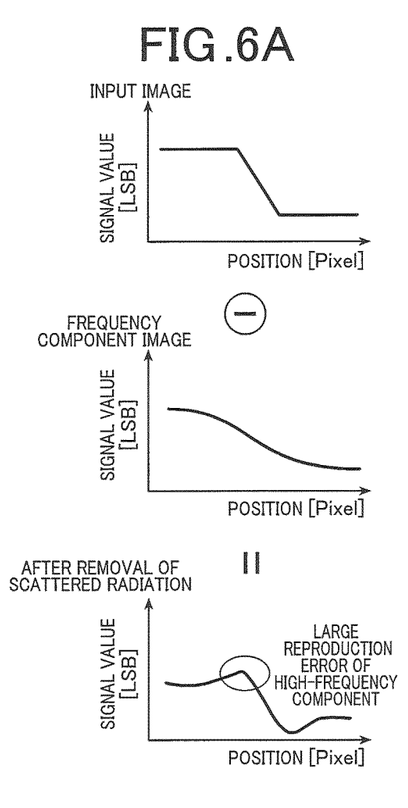
FIG. 6A is a view illustrating a result of scattered radiation removal based on a frequency component image obtained by performing filter processing using a constant weighting factor.
Figure 6B:
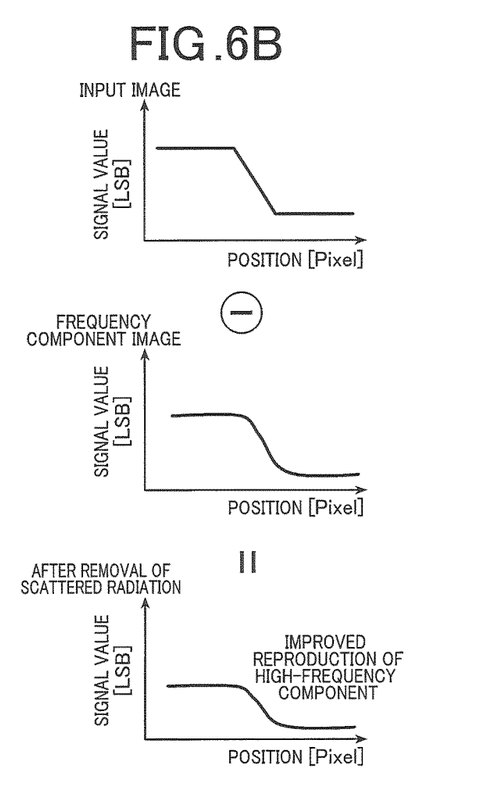
FIG. 6B is a view illustrating a result of scattered radiation removal based on a frequency component image obtained by performing filter processing using a weighting factor reflecting the edge.

FIG. 6A is a view illustrating a result of the scattered radiation removal based on a frequency component image obtained by performing filter processing on a radiographic image using a constant weighting factor. FIG. 6B is a view illustrating a result of the scattered radiation removal based on a frequency component image obtained by performing filter processing on a radiographic image using a weighting factor reflecting the edge intensity (in which the weighting factor becomes smaller as the edge becomes stronger). As illustrated in FIG. 6A, when the weighting factor is constant irrespective of the edge intensity, the accuracy in estimating the scattered radiation becomes worse as the edge is stronger. Therefore, reproduction errors of high-frequency components in the vicinity of edges occur in the radiographic image from which the scattered radiation has been removed. On the other hand, as illustrated in FIG. 6B, performing the filter processing while setting the weighting factor of the kernel to be used in the filter processing to become smaller as the edge becomes stronger can improve the accuracy in estimating high-frequency components of the scattered radiation for the portion where the edge is strong and can accurately remove the scattered radiation.

Second Exemplary Embodiment

Next, a second exemplary embodiment of the present invention will be described.

Since the second exemplary embodiment is similar to the first exemplary embodiment in its configuration and imaging operation, their descriptions will be cited. Hereinafter, operations that can be performed by the console 2 according to the second exemplary embodiment will be described.

Figure 7:
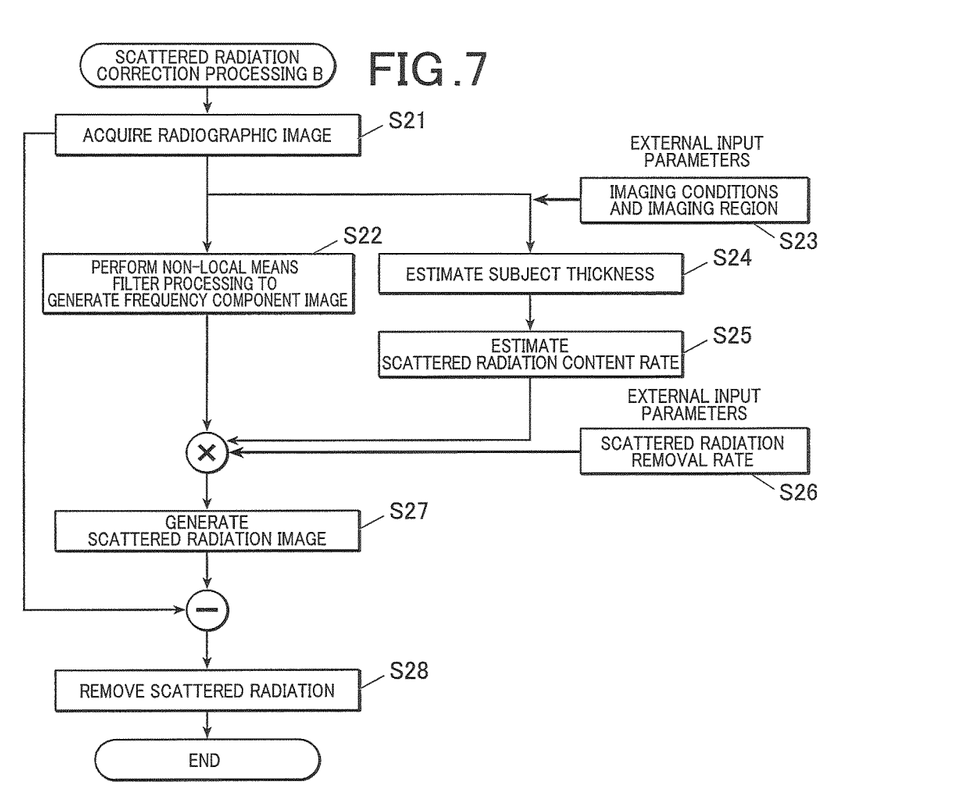
FIG. 7 is a view schematically illustrating an exemplary flow of scattered radiation correction processing B that can be executed by the controller illustrated in FIG. 2 according to a second exemplary embodiment.

In the console 2, when receiving image data from the radiation detector P, the controller 21 executes scattered radiation correction processing B. FIG. 7 is a flowchart illustrating an exemplary flow of the scattered radiation correction processing B. The scattered radiation correction processing B can be executed by cooperation between the controller 21 and the programs stored in the storage device 22.

First, the controller 21 acquires a radiographic image transmitted from the radiation detector P via the communication device 25 (step S21).

Next, the controller 21 performs non-local means (NLM) filter processing on the radiographic image to generate a frequency component image (step S22).

The non-local means filter is a filter that performs smoothing while preserving edges by using a calculation result of the degree of similarity of a local image as a weighting factor at the time of the convolution calculation.

Figure 8:
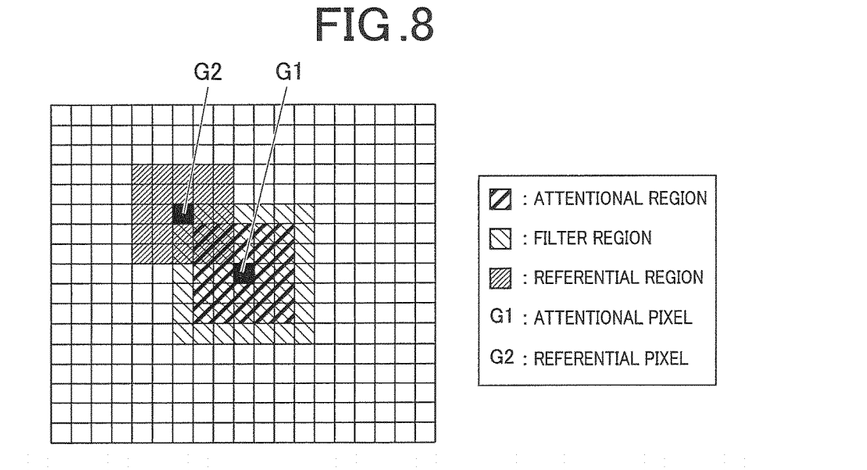
FIG. 8 is a view illustrating exemplary non-local means filter processing.

The non-local means filter processing will be described below with reference to FIG. 8. The following (1) to (6) is processing to be executed while designating each pixel of the radiographic image as an attentional pixel G1, in the non-local means filter processing.

(1) The controller 21 sets a region of m pixels×n pixels (m and n are positive integers) including the attentional pixel G1 positioned at the center thereof as an attentional region.
(2) The controller 21 sets a filter region around the attentional region (including the attentional region).
(3) The controller 21 designates each pixel in the filter region as a referential pixel G2, and sets a region of m pixels×n pixels (m and n are positive integers) including the referential pixel G2 positioned at the center thereof as a referential region.
(4) The controller 21 calculates the degree of similarity between the attentional region and the referential region. For example, the square sum of the difference between the pixel value of each pixel in the attentional region and the pixel value of the corresponding position in the referential region can be calculated as the degree of similarity between the attentional region and the referential region, although it is not limited specifically. In this case, the controller 21 can determine that the edge is stronger as the degree of similarity between the attentional region and the referential region is lower. Therefore, in the present exemplary embodiment, the calculated degree of similarity can be used as a determination result of the edge intensity.
(5) The controller 21 calculates a weighted average of respective pixels in the filter region while designating the calculated degree of similarity as a weighting factor of the referential pixel G2.
(6) The controller 21 replaces the value of the attentional pixel G1 with the calculated weighted average. By executing the processing of (1) to (6) for all pixels, the controller 21 generates the frequency component image.

In the filter processing, since the frequency band of a filter processed image is determined by the kernel, performing the filter processing using a weighting factor based on the edge determination result as the kernel can change the frequency band to be extracted by the location in the radiographic image (the intensity of the edge at the location).

Next, the controller 21 acquires imaging conditions of the radiographic image and imaging region information as external parameters (step S23), and estimates the subject thickness from the radiographic image based on the acquired imaging conditions (step S24), and further estimates a scattered radiation content rate from the radiographic image based on the acquired imaging region and the estimated subject thickness (step S25). The processing in steps S23 to S25 may be executed concurrently with the processing in step S22 or may be executed earlier.

Next, the controller 21 acquires a scattered radiation removal rate as an external parameter (step S26).

Next, the controller 21 multiplies each pixel in the frequency component image generated in step S22 by the scattered radiation content rate to estimate a scattered radiation component and multiplies the scattered radiation component by the scattered radiation removal rate to generate a scattered radiation image representing the scattered radiation amount to be removed from the radiographic image (step S27).

Then, the controller 21 subtracts the scattered radiation image from the radiographic image to generate a radiographic image from which the scattered radiation has been removed (step S28), and terminates the scattered radiation correction processing B.

In the second exemplary embodiment, similar to the first exemplary embodiment, by performing the filter processing on the radiographic image with the weighting factor becoming smaller as the edge becomes stronger (as the degree of similarity becomes smaller), the accuracy in estimating high-frequency components of the scattered radiation can be improved for strong edge portions, and the scattered radiation can be accurately removed.

Third Exemplary Embodiment

Next, a third exemplary embodiment of the present invention will be described.

Since the third exemplary embodiment is similar to the first exemplary embodiment in its configuration and imaging operation, their descriptions will be cited. Hereinafter, operations that can be performed by the console 2 according to the third exemplary embodiment will be described.

Figure 9:
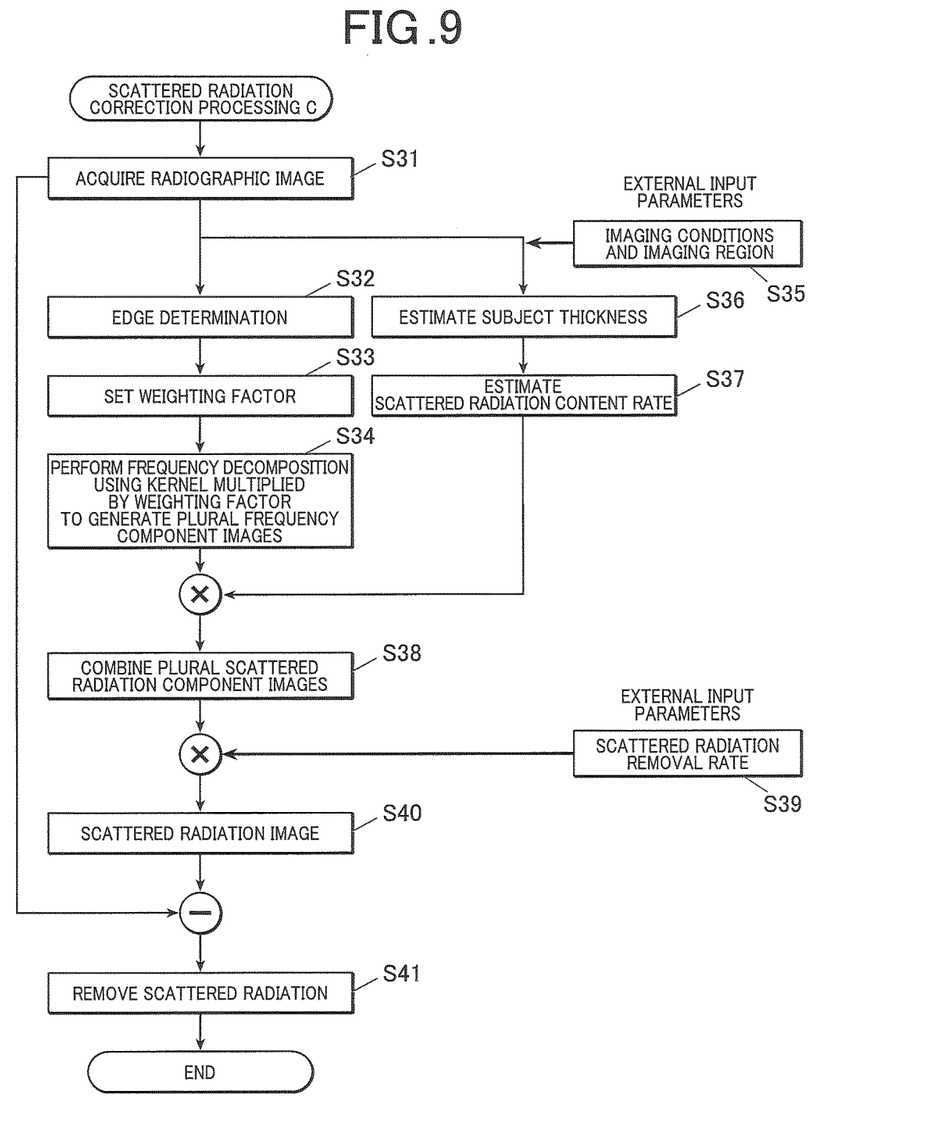
FIG. 9 is a view schematically illustrating an exemplary flow of scattered radiation correction processing C that can be executed by the controller illustrated in FIG. 2 according to a third exemplary embodiment.

In the console 2, when receiving image data from the radiation detector P, the controller 21 executes scattered radiation correction processing C. FIG. 9 is a flowchart illustrating an exemplary flow of the scattered radiation correction processing C. The scattered radiation correction processing C can be executed by cooperation between the controller 21 and the programs stored in the storage device 22.

First, the controller 21 acquires a radiographic image transmitted from the radiation detector P via the communication device 25 (step S31).

Next, the controller 21 performs edge determination processing on the radiographic image (step S32).

The edge determination processing in step S32 is, for example, the edge determination processing (including the one using the variance value) described in step S2 in FIG. 3 or the edge determination processing using the degree of similarity calculated through the processing of (1) to (4) described in step S22 of FIG. 7, or the like.

Next, the controller 21 sets a weighting factor to be used in the convolution calculation during the filter processing based on the edge determination result (step S33).

In step S33, the controller 21 sets the weighting factor for the referential pixel in each edge determination region. In the present embodiment, the setting of the weighting factor is performed in such a manner that the weighting factor becomes smaller as the edge is weaker or when there is no edge (as the difference or ratio in pixel value between the attentional pixel and the referential pixel calculated in the edge determination processing is smaller, the variance value is smaller, or the degree of similarity is larger) and becomes larger as the edge is stronger (as the difference or ratio in pixel value between the attentional pixel and the referential pixel calculated in edge determination processing is larger, the variance value is larger, or the degree of similarity is smaller). In the storage device 22, the difference in pixel value between the attentional pixel and the referential pixel (or the ratio, the variance value or the degree of similarity) is stored beforehand in relation to the weighting factor.

Next, the controller 21 performs frequency decomposition on the radiographic image using the weighting factor having been set and generates frequency component images of a plurality of frequency bands (a plurality of frequency band images) (step S34).

For example, one of the following (A) and (B) is employable as the method of frequency decomposition.

(A) Using a kernel being constant in size and shape to generate frequency component image of a plurality of frequency bands.

(B) Using kernels differentiated in size and/or shape to generate frequency component image of a plurality of frequency bands.

Figure 10:
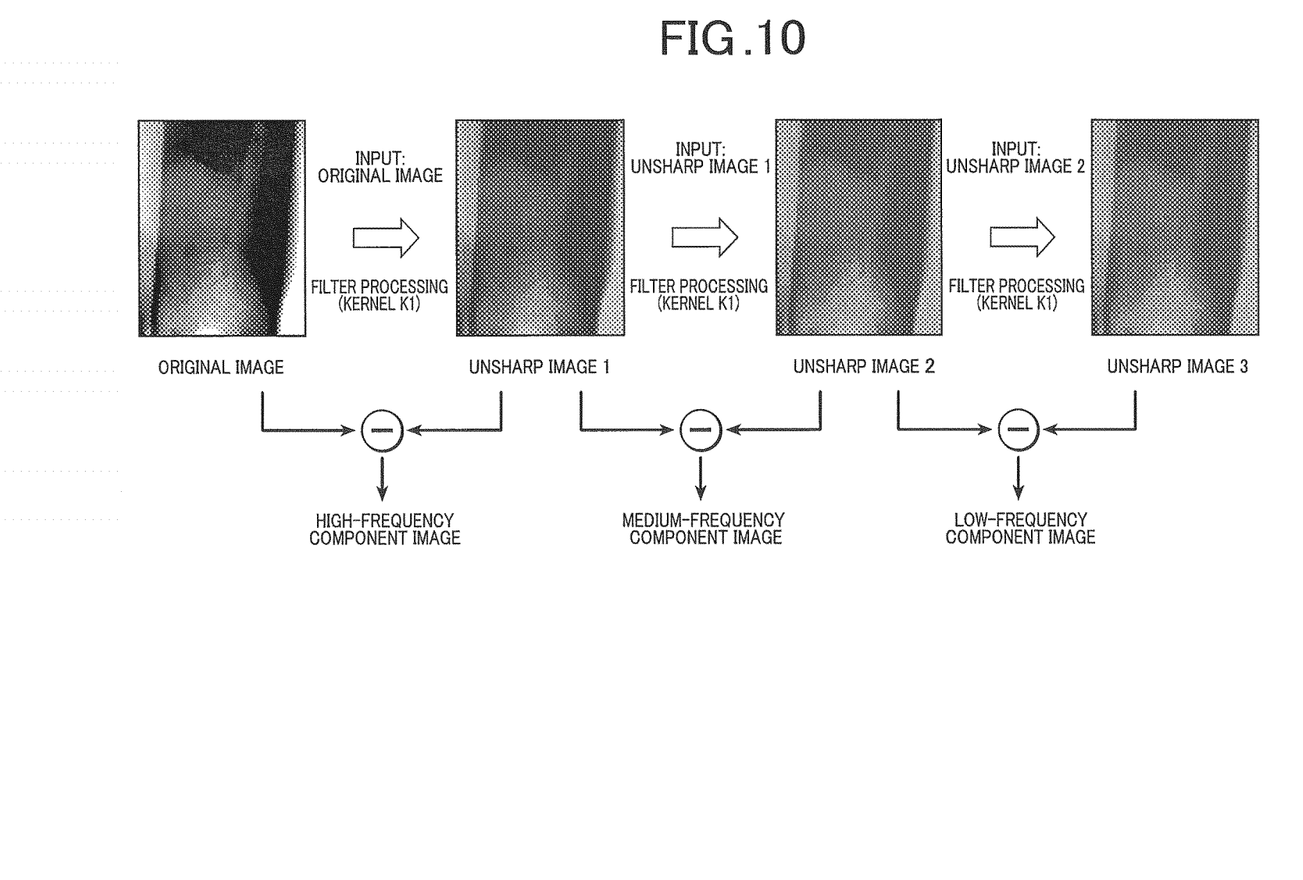
FIG. 10 is a view illustrating frequency decomposition using only one kernel.

According to above-mentioned method (A), for example, as illustrated in FIG. 10, the controller 21 first generates an unsharp image 1 by performing filter processing (e.g., a simple averaging filter, a binominal filter, a Gaussian filter, or the like) on an input radiographic image (an original image) using a kernel K1 being constant in size and shape, which is prepared beforehand (stored in the storage device 22). Then, the controller 21 performs filter processing on the unsharp image 1 using the kernel K1 to generate an unsharp image 2. Next, the controller 21 performs filter processing on the unsharp image 2 using the kernel K1 to generate an unsharp image 3. Then, the controller 21 generates a high-frequency component image by obtaining a difference between the original image and the unsharp image 1, a medium-frequency component image by obtaining a difference between the unsharp image 1 and the unsharp image 2, and a low-frequency component image by obtaining a difference between the unsharp image 2 and the unsharp image 3.

Namely, in step S34, the controller 21 generates a plurality of unsharp images by performing filter processing using a kernel obtained by multiplying the kernel K1 having been set beforehand by the weighting factor set in step S33, and generates a plurality of frequency band images (e.g., high-frequency component image, medium-frequency component image, and low-frequency component image) using the plurality of generated unsharp images.

Figure 11:
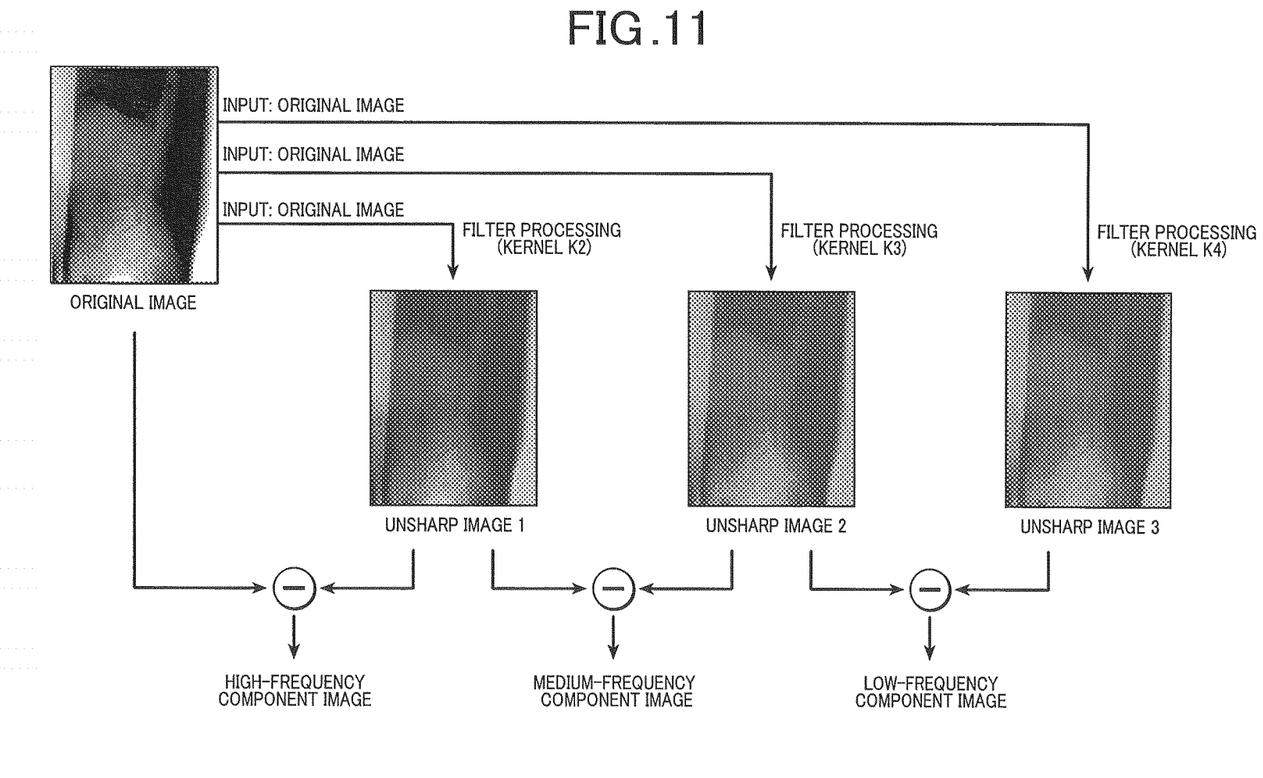
FIG. 11 is a view illustrating frequency decomposition using a plurality of kernels that are mutually different in size and/or shape.

According to above-mentioned method (B), for example, as illustrated in FIG. 11, the controller 21 performs filter processing (for example, the simple averaging filter, the binominal filter, the Gaussian filter, or the like) on an original image using kernels K2 to K4 differentiated in size and/or shape to generate a plurality of unsharp images 1 to 3 different in frequency band. Then, the controller 21 generates a high-frequency component image by obtaining a difference between the original image and the unsharp image 1, a medium-frequency component image by obtaining a difference between the unsharp image 1 and the unsharp image 2, and a low-frequency component image by obtaining a difference between the unsharp image 2 and the unsharp image 3.

Namely, in step S34, the controller 21 generates a plurality of unsharp images by performing filter processing using kernels obtained by multiplying the kernels K2 to K4 having been set beforehand by the weighting factor set in step S33, and generates frequency component images of a plurality of frequency bands (e.g., high-frequency component image, medium-frequency component image, and low-frequency component image) using the generated plurality of unsharp images.

In the description of (A) and (B) using FIG. 10 and FIG. 11, although three unsharp images are generated to generate frequency component images of three frequency bands (high-frequency component image, medium-frequency component image, and low-frequency component image), this is only an example. Frequency component images of a plurality of necessary bands can be generated by generating a plurality of unsharp images and obtaining their differences.

When the filter processing is performed using kernels different in size, it is feasible to extract different frequency components according to the size of each kernel. The larger the kernel size is, the higher the effect of smoothing is. This is useful in extracting low-frequency components. The smaller the kernel size is, the lower the effect of smoothing is. This is useful in extracting high-frequency components. More specifically, when the kernels K2 to K4 are differentiated in size, the size of kernel K2<the size of kernel K3<the size of kernel K4.

Figure 12A:
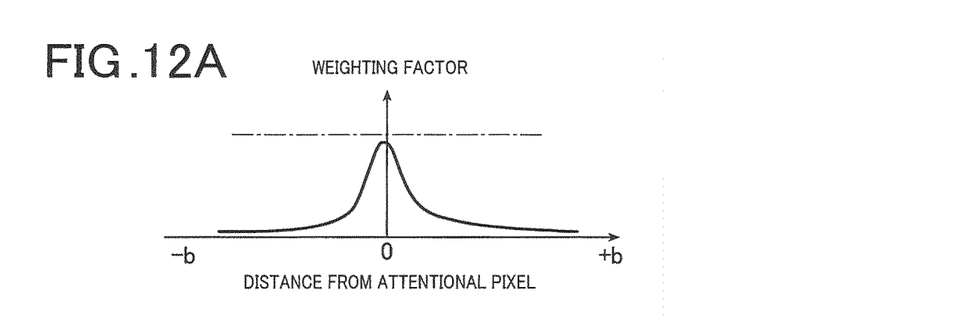
FIG. 12A is a view illustrating an exemplary relationship between the distance from an attentional pixel and the weighting factor in a kernel to be used in the frequency decomposition and differentiated in shape.
Figure 12B:
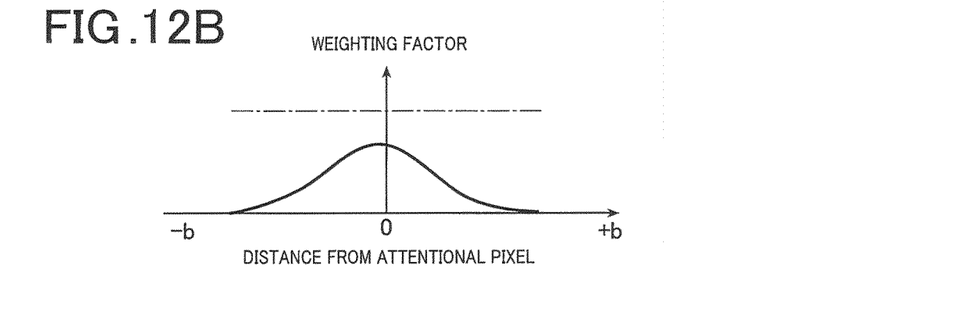
FIG. 12B is a view illustrating an exemplary relationship between the distance from an attentional pixel and the weighting factor in another kernel to be used in the frequency decomposition and differentiated in shape.
Figure 12C:
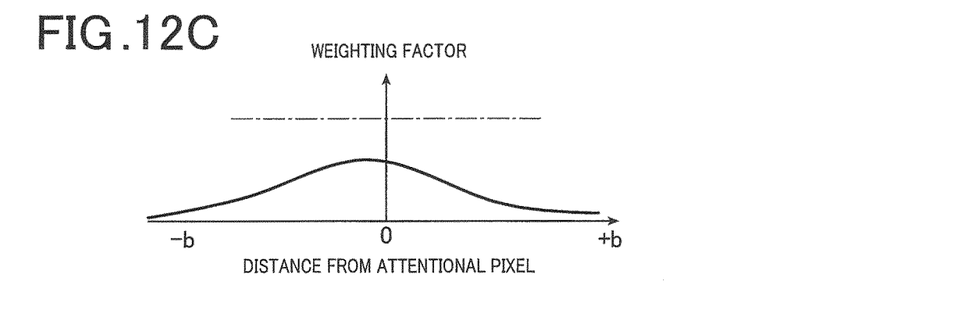
FIG. 12C is a view illustrating an exemplary relationship between the distance from an attentional pixel and the weighting factor in another kernel to be used in the frequency decomposition and differentiated in shape.
Figure 12D:
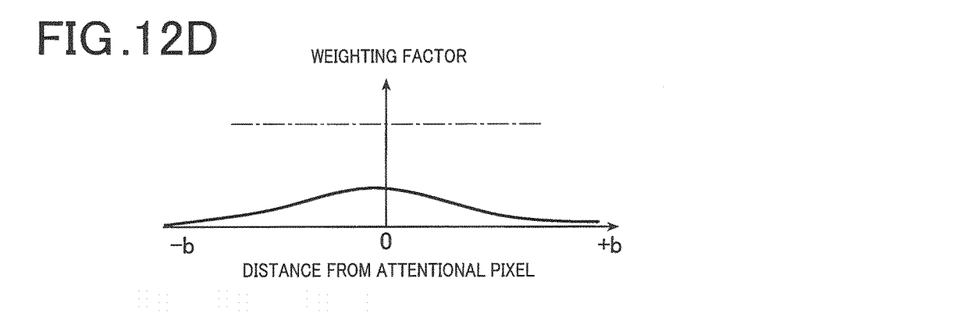
FIG. 12D is a view illustrating an exemplary relationship between the distance from an attentional pixel and the weighting factor in another kernel to be used in the frequency decomposition and differentiated in shape.

Further, when the filter processing is performed using kernels different in shape, it is feasible to extract different frequency components according to the shape of each kernel. The kernels different in shape are, for example, kernels different in weighting factor to be multiplied with the filter factor having been set beforehand according to the distance between the attentional pixel and the referential pixel. FIG. 12A to FIG. 12D illustrate examples of the weighting factor. As illustrated in FIG. 12A, when using a kernel whose weighting factor changes steeply as the distance from the attentional pixel is shorter, the effect of smoothing is lower and accordingly high-frequency components can be extracted. As illustrated in FIG. 12D, when using a kernel whose weighting factor changes gradually according to the distance from the attentional pixel, the effect of smoothing is higher and accordingly low-frequency components can be extracted.

The frequency bands of the frequency components to be extracted in step S34 and the kernels to be used in extracting the frequency component images are set (stored in the storage device 22) beforehand based on experiments.

Next, the controller 21 acquires imaging conditions of the radiographic image and imaging region information as external parameters (step S35), and estimates the subject thickness from the radiographic image based on the acquired imaging conditions (step S36), and further estimates a scattered radiation content rate from the radiographic image based on the acquired imaging region and the estimated subject thickness (step S37). The processing in steps S35 to S37 may be executed concurrently with the processing in steps S32 to S34 or may be executed earlier.

Next, the controller 21 multiplies each pixel of the frequency component image of each frequency band generated in step S34 by the scattered radiation content rate to generate a scattered radiation component image estimating the scattered radiation component of each frequency band, and then combines them (step S38).

Next, the controller 21 acquires a scattered radiation removal rate as an external parameter (step S39), and multiplies the combined scattered radiation component image by the scattered radiation removal rate to generate a scattered radiation image indicating the scattered radiation amount to be removed (step S40).

Then, the controller 21 subtracts the scattered radiation image from the radiographic image to generate a radiographic image from which the scattered radiation has been removed (step S41), and terminates the scattered radiation correction processing C.

In the third exemplary embodiment, the radiographic image is designated as the original image, the filter processing is repetitively performed using the kernel whose weighting factor becomes larger as the edge is stronger to generate unsharp images of a plurality of frequency bands, and the generated unsharp images are subtracted from the original image to generate frequency band images of the plurality of frequency bands. Accordingly, it is feasible to extract high-frequency components of the scattered radiation for strong edge portions. The accuracy in estimating high-frequency components of the scattered radiation can be improved for strong edge portions, and the scattered radiation can be accurately removed. Further, compared to the first and second exemplary embodiments, the third exemplary embodiment brings an effect that it is easy to extract the scattered radiation of an aimed frequency component.

Fourth Exemplary Embodiment

Next, a fourth exemplary embodiment of the present invention will be described.

Since the fourth exemplary embodiment is similar to the first exemplary embodiment in its configuration and imaging operation, their descriptions will be cited. Hereinafter, operations that can be performed by the console 2 according to the fourth exemplary embodiment will be described.

Figure 13:
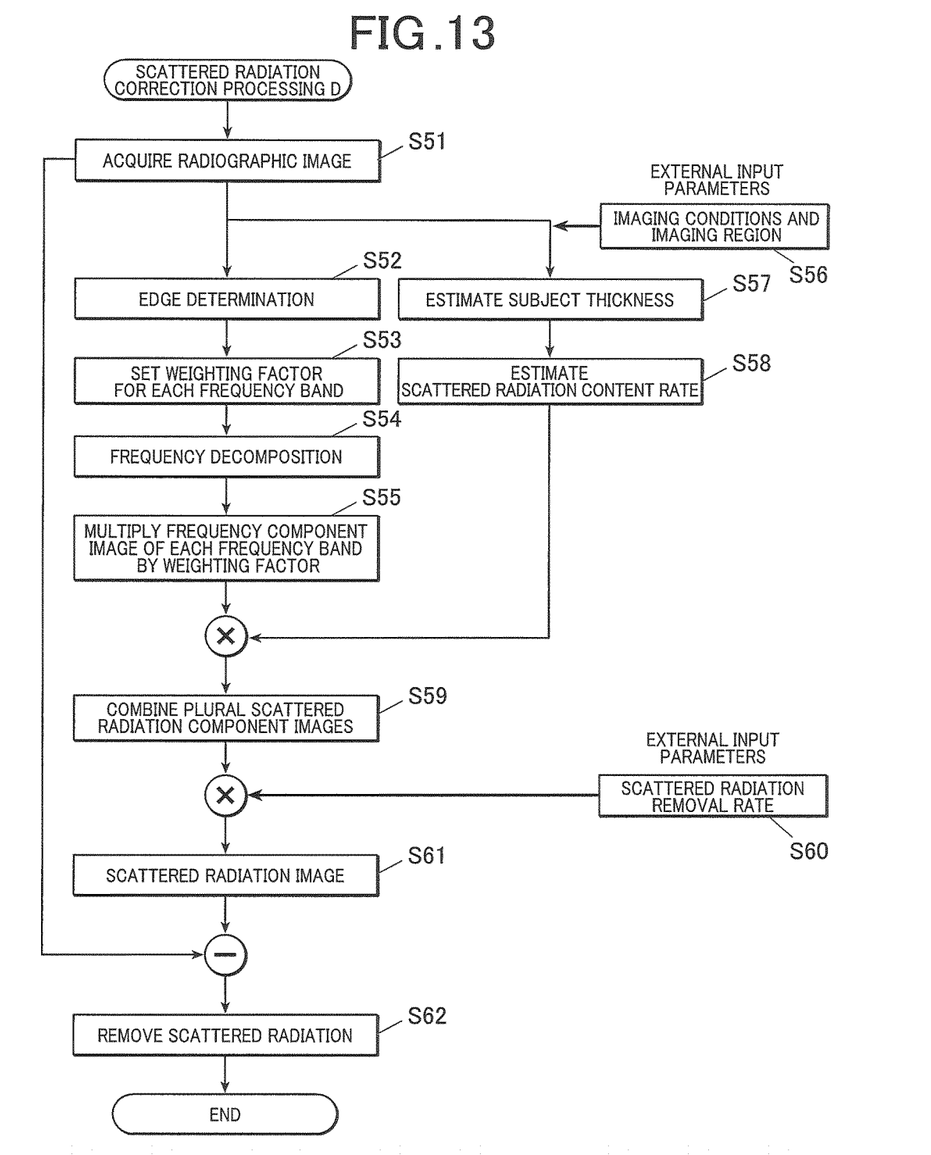
FIG. 13 is a view schematically illustrating an exemplary flow of scattered radiation correction processing D that can be executed by the controller illustrated in FIG. 2 according to a fourth exemplary embodiment.

In the console 2, when receiving image data from the radiation detector P, the controller 21 executes scattered radiation correction processing D. FIG. 13 is a flowchart illustrating an exemplary flow of the scattered radiation correction processing D. The scattered radiation correction processing D can be executed by cooperation between the controller 21 and the programs stored in the storage device 22.

First, the controller 21 acquires a radiographic image transmitted from the radiation detector P via the communication device 25 (step S51).

Next, the controller 21 performs edge determination processing on the radiographic image (step S52).

In step S52, first, the controller 21 designates each pixel of the radiographic image as an attentional pixel, and sets a region of m pixels×n pixels (m and n are positive integers) including the attentional pixel positioned at the center thereof as an edge determination region. Next, in each edge determination region, the controller 21 calculates a variance value of the pixel value in the region and determines the edge intensity based on the variance value. For example, the controller 21 determines that the edge is stronger as the variance value is larger and the edge is weaker as the variance value is smaller. Alternatively, the controller 21 may obtain a difference or ratio between an average of respective pixel values in the edge determination region and the pixel value of the attentional pixel, and may determine that the edge is stranger as the difference or ratio is larger and weaker as the difference or ratio is smaller.

Next, the controller 21 sets a weighting factor to be used for a frequency component image of each frequency band to be generated in step S54, for each pixel, based on the edge determination result (step S53). For example, the setting of the weighting factor is performed in such a manner that the weighting factor applied to the frequency component image of the high-frequency band becomes larger as the peripheral edge of the pixel is stronger and the weighting factor applied to the frequency component image of the low-frequency band becomes smaller as the peripheral edge of the pixel is weaker. The relationship between the edge intensity (variance value) and the weighting factor applied to the frequency component image of each frequency band is determined based on experiments and stored beforehand in the storage device 22.

Next, the controller 21 performs frequency decomposition on the radiographic image and generates frequency component images of a plurality of frequency bands (step S54).

In step S54, for example, the controller 21 performs the frequency decomposition according to the method (A) or (B) described in step S34 of the scattered radiation correction processing C according to the third exemplary embodiment. In this step S54, the controller 21 does not use the weighting factor set in step S53.

Next, the controller 21 multiplies each of the generated frequency component images of the plurality of frequency bands by the weighting factor set in step S53 to generate a plurality of weighted frequency component images (step S55).

Next, the controller 21 acquires imaging conditions of the radiographic image and imaging region information as external parameters (step S56), and estimates the subject thickness from the radiographic image based on the acquired imaging conditions (step S57), and further estimates a scattered radiation content rate from the radiographic image based on the acquired imaging region and the estimated subject thickness (step S58). The processing in steps S56 to S58 may be executed concurrently with the processing in steps S52 to S55 or may be executed earlier.

Next, the controller 21 multiplies each pixel of the frequency component image of each frequency band, to which the weighting factor has been multiplied in step S55, by the scattered radiation content rate to generate a scattered radiation component image estimating the scattered radiation component of each frequency band, and then combines them (step S59).

Next, the controller 21 acquires a scattered radiation removal rate as an external parameter (step S60), multiplies the combined scattered radiation component image by the scattered radiation removal rate to generate a scattered radiation image indicating the scattered radiation amount to be removed (step S61).

Then, the controller 21 subtracts the scattered radiation image from the radiographic image to generate a radiographic image from which the scattered radiation has been removed (step S62), and terminates the scattered radiation correction processing D.

In the fourth exemplary embodiment, the weight of the high-frequency band image included in the scattered radiation image to be used in estimating the scattered radiation becomes stranger as the edge in the region is stronger. Therefore, the accuracy in estimating high-frequency components of the scattered radiation can be improved for strong edge portions, and the scattered radiation can be accurately removed. Further, compared to the first and second exemplary embodiments, the fourth exemplary embodiment brings an effect that it is easy to extract the scattered radiation of an aimed frequency component.

As mentioned above, the controller 21 of the console 2 determines the intensity of an edge in a radiographic image obtained by radiographically imaging a subject, sets a weighting factor to be used in extracting a frequency component of a predetermined frequency band from the radiographic image according to a determination result, extracts the frequency component from the radiographic image using the weighting factor having been set, and multiplies the extracted frequency component by the scattered radiation content rate to estimate the scattered radiation component in radiographic image. Then, the controller 21 multiplies the estimated scattered radiation component by the scattered radiation removal rate to generate the scattered radiation image representing the scattered radiation component to be removed from the radiographic image, and performs scattered radiation correction on the radiographic image by subtracting the scattered radiation image from the radiographic image.

Accordingly, it is feasible to improve the accuracy in estimating the scattered radiation in the vicinity of edges in the radiographic image, and therefore it is feasible to obtain a radiographic image from which the scattered radiation has been precisely removed.

The contents described in the above-mentioned exemplary embodiments are preferred examples, and the present invention is not limited to these examples.

For example, in the above-mentioned exemplary embodiments, the present invention is applied to a radiographic image of a chest. However, the present invention is also applicable to a radiographic image capturing another region.

Further, in the above-mentioned exemplary embodiments, the console 2 controlling the image capturing apparatus 1 is functionally operable as the radiographic image processing apparatus. However, the radiographic image processing apparatus may be separated from the console.

Further, for example, in the above-mentioned description, the hard disk and the semiconductor nonvolatile memory are practical examples of a computer readable medium storing the programs according to the present invention. However, the computer readable medium is not limited to these examples. For example, a portable storage medium such as a compact disk read only memory (CD-ROM) is employable as a computer readable medium. Further, carrier waves are employable as a medium capable of providing data of the programs according to the present invention via a communication line.

Further, detailed configurations and detailed operations of respective devices constituting the radiographic imaging system can be appropriately modified without departing from the gist of the present invention.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese Patent Application No. 2018-009644 filed on Jan. 24, 2018 including the specification, claims, drawings, and abstract is incorporated herein by reference in its entirety.

What is claimed is:

1. A radiographic image processing apparatus comprising a hardware processor, which
    determines the intensity of an edge in a radiographic image obtained by radiographically imaging a subject,
    sets a weighting factor to be used in extracting a frequency component from the radiographic image according to a determination result of the edge intensity,
    extracts the frequency component from the radiographic image using the weighting factor having been set,
    multiplies the extracted frequency component by a scattered radiation content rate to estimate a scattered radiation component in the radiographic image,
    multiplies the estimated scattered radiation component by a scattered radiation removal rate to generate a scattered radiation image representing the scattered radiation component to be removed from the radiographic image, and performs scattered radiation correction on the radiographic image by subtracting the scattered radiation image from the radiographic image.

2. The radiographic image processing apparatus according to claim 1, wherein the hardware processor sets each pixel of the radiographic image as an attentional pixel and sets a plurality of pixels around the attentional pixel as referential pixels, calculates a difference or a ratio in pixel value between each referential pixel and the attentional pixel, and determines the intensity of an edge around the attentional pixel based on the magnitude of the calculated difference or ratio.

3. The radiographic image processing apparatus according to claim 1, wherein the hardware processor sets each pixel of the radiographic image as an attentional pixel and sets a region of a plurality of peripheral pixels including the attentional pixel positioned at the center thereof as an attentional region, and determines the intensity of an edge around the attentional pixel based on a calculation result of the degree of similarity between the attentional region and a peripheral referential region.

4. The radiographic image processing apparatus according to claim 1, wherein the hardware processor sets each pixel of the radiographic image as an attentional pixel and sets an edge determination region including a plurality of pixels and the attentional pixel positioned at the center thereof, and determines the intensity of an edge around the attentional pixel based on a variance value of a pixel value in the edge determination region.

5. The radiographic image processing apparatus according to claim 1, wherein the hardware processor sets a larger weighting factor as the edge having been determined is weaker and sets a smaller weighting factor as the edge having been determined is stronger, and extracts the frequency component from the radiographic image by performing filter processing on the radiographic image using a kernel generated by using the weighting factor having been set.

6. The radiographic image processing apparatus according to claim 1, wherein the hardware processor sets a smaller weighting factor as the edge having been determined is weaker and sets a large weighting factor as the edge having been determined is stronger, and extracts frequency components of a plurality of frequency bands by performing frequency decomposition on the radiographic image using a kernel generated by using the weighting factor having been set.

7. The radiographic image processing apparatus according to claim 1, wherein the hardware processor sets the weighting factor for each frequency band in such a way as to set a larger weighting factor applied to a frequency component of a high-frequency band as the edge having been determined is stronger and set a larger weighting factor applied to a frequency component of a low-frequency band as the edge having been determined is weaker, extracts frequency components of a plurality of frequency bands by performing frequency decomposition on the radiographic image using a kernel prepared beforehand and being constant in size and shape or a plurality of kernels prepared beforehand and differentiated in size and/or shape, and multiplies each of the extracted frequency components of the plurality of frequency bands by the weighting factor having been set.

8. A scattered radiation correction method for a radiographic image processing apparatus that performs scattered radiation correction on a radiographic image obtained by radiographically imaging a subject, the method comprising:

determining the intensity of an edge in the radiographic image;

setting a weighting factor to be used in extracting a frequency component from the radiographic image according to a determination result of the edge intensity;

extracting the frequency component from the radiographic image using the weighting factor having been set;

multiplying the extracted frequency component by a scattered radiation content rate to estimate a scattered radiation component in the radiographic image;

multiplying the estimated scattered radiation component by a scattered radiation removal rate to generate a scattered radiation image representing the scattered radiation component to be removed from the radiographic image; and performs scattered radiation correction on the radiographic image by subtracting the scattered radiation image from the radiographic image.

9. A non-transitory computer readable storage medium storing a program that causes a computer, to be used for a radiographic image processing apparatus that performs scattered radiation correction on a radiographic image obtained by radiographically imaging a subject, to determine the intensity of an edge in the radiographic image obtained by radiographically imaging the subject, set a weighting factor to be used in extracting a frequency component from the radiographic image according to a determination result of the edge intensity, extract the frequency component from the radiographic image using the weighting factor having been set, multiply the extracted frequency component by a scattered radiation content rate to estimate a scattered radiation component in the radiographic image, multiply the estimated scattered radiation component by a scattered radiation removal rate to generate a scattered radiation image representing the scattered radiation component to be removed from the radiographic image, and perform scattered radiation correction on the radiographic image by subtracting the scattered radiation image from the radiographic image.

* * * * *